United States Patent [19]
Skribiski

[11] Patent Number: 4,867,174
[45] Date of Patent: Sep. 19, 1989

[54] GUIDEWIRE FOR MEDICAL USE

[75] Inventor: Robert P. Skribiski, Irvine, Calif.

[73] Assignee: Baxter Travenol Laboratories, Inc., Deerfield, Ill.

[21] Appl. No.: 122,211

[22] Filed: Nov. 18, 1987

[51] Int. Cl.$^4$ .............................................. A61M 25/00
[52] U.S. Cl. ..................................... 128/772; 128/657
[58] Field of Search ........................ 128/772, 656–658, 128/341; 604/95, 170, 280; 428/36

[56]  References Cited

U.S. PATENT DOCUMENTS

| | | |
|---|---|---|
| 3,789,841 | 2/1974 | Antoshkiw ........................ 128/772 |
| 3,802,440 | 4/1974 | Salem et al. . |
| 3,924,632 | 12/1975 | Cook . |
| 3,941,119 | 3/1976 | Corrales . |
| 3,973,556 | 8/1976 | Fleishhacker et al. . |
| 4,020,829 | 5/1977 | Willson et al. . |
| 4,085,757 | 4/1978 | Pevsner . |
| 4,169,464 | 10/1979 | Obrez . |
| 4,204,528 | 5/1980 | Termanini . |
| 4,211,741 | 7/1980 | Ostoich . |
| 4,257,421 | 3/1981 | Beal . |
| 4,283,447 | 8/1981 | Flynn . |
| 4,345,602 | 8/1982 | Yoshimura et al. . |
| 4,385,635 | 5/1983 | Ruiz . |
| 4,419,095 | 12/1983 | Nebergall et al. . |
| 4,425,919 | 1/1984 | Alston, Jr. et al. . |
| 4,464,176 | 8/1984 | Wijayarathna . |
| 4,504,268 | 3/1985 | Herlitze . |
| 4,531,943 | 7/1985 | Van Tassel et al. . |
| 4,563,181 | 1/1986 | Wijayarathna et al. . |
| 4,682,607 | 7/1987 | Vaillancourt et al. .............. 128/772 |

FOREIGN PATENT DOCUMENTS

| | | |
|---|---|---|
| 0014424 | 8/1980 | European Pat. Off. . |
| 3109402 | 3/1981 | Fed. Rep. of Germany . |
| 2017182 | 10/1979 | United Kingdom . |

OTHER PUBLICATIONS

"Thermoplastic Polyester", Bennett Nathanson, Modern Plastics Encyclopedia, pp. 42–50, 1985–1986.
"Angiography and Its Latest Aspects", M. H. Wholey, 1972.

*Primary Examiner*—Stephen C. Pellegrino
*Attorney, Agent, or Firm*—Gordon L. Peterson; Frank J. Uxa, Jr.

[57]  ABSTRACT

A structure comprising: an elongated, flexible inner element and a substantially water insoluble, biocompatible sheath disposed over the inner element, the structure having a substantially uniform cross-section, being substantially solid, and sized and shaped for insertion into the body of a medical patient, the inner element having a reduced tendency to creep relative to the sheath, and the sheath having increased softness relative to the inner element.

29 Claims, 2 Drawing Sheets

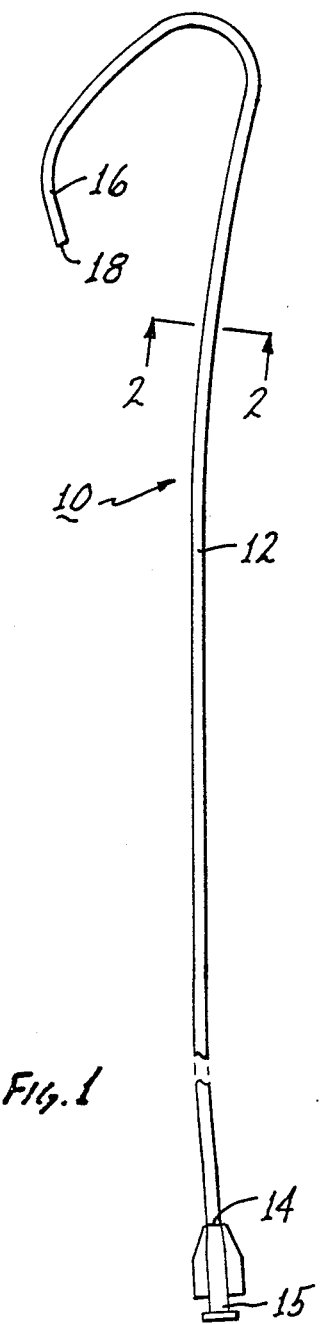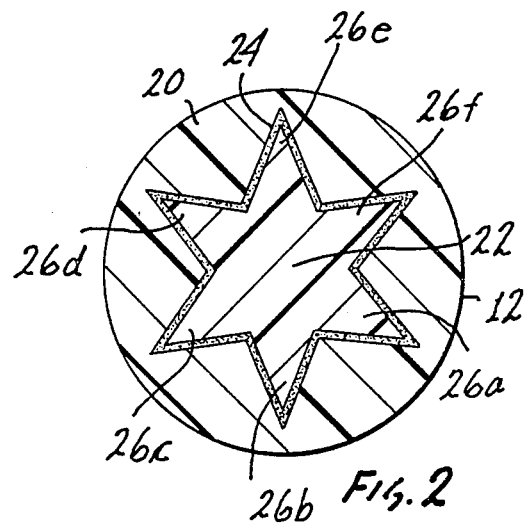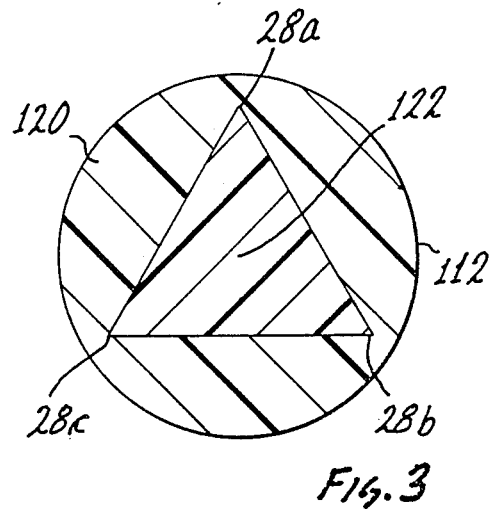

4,867,174

GUIDEWIRE FOR MEDICAL USE

BACKGROUND OF THE INVENTION

This invention relates to a structure useful as a guidewire for medical purposes. More particularly, the invention relates to a structure with anti-creep properties and suitable softness, and preferably substantial torque control, usable as a guidewire in connection with medical treatments.

Guidewires are often utilized in placing catheters and other implements into the bodies, e.g., blood vessels, various cavities and the like, of medical patients. Such guidewires may have to be manipulated through long and tortuous paths. They must have sufficient column strength to be able to direct the implement to be placed in the patient's body while,. at the same time, being flexible enough to negotiate the often tortuous path and being soft enough to avoid unduly damaging or injuring the path.

One problem which has plagued guidewire constructions, especially all plastic guidewire constructions, is the phenomenon called "creep". This is defined as the susceptibility of a material, e.g., a plastic material, to become deformed by the application of a low level force over a long period of time. An example of this creep property is the "set" that plastic tubing often assumes after being coiled in a box. Upon removal from the box, the length of tubing will maintain its coiled configuration to some extent. It is desirable, e.g., in order that the guidewire have good ability to be deformed as desired to pass through the body, that the guidewire has a reduced tendency to creep or an enhanced anti-creep property.

The term "torque control" as used herein refers to the ability of a guidewire to transmit twisting forces along its length, and satisfactory guidewire performance often depends on this ability. Satisfactory torque control enables carefully controlled maneuvering of the guidewire within the patient's body by skilled manipulations at the guidewire's proximal end. Thus, torque control is important and increases in torque control are advantageous.

A number of guidewire constructions have previously been suggested. For example, Herlitze U.S. Pat. No. 4,504,268 discloses a stiffening rod for a catheter comprising at least one resilient, high tensile strength multifilament strand, made of non-rusting steel, embedded in a plastic rod having a high percentage of x-ray contrast material to make it easier to detect the catheter by x-ray. Herlitze teaches that the high tensile strength filaments, which are placed in the center of the stiffener without being bound together, impart high tensile strength to the rod and reduce the probability of the rod breaking. However, since the filaments are separate and not a unitary structure, torque control of the Herlitze stiffener may not be acceptable. Also, since the filaments are not bound together, hollow areas and inconsistencies in strength, i.e., weak spots, along the length of the stiffener may be troublesome. Herlitze is concerned with x-ray detection of the catheter and not with the anti-creep properties or torque control of the stiffener.

Yoshimura, et al U.S. Pat. No. 4,345,602 discloses a vascular guidewire which has a varied structure, i.e., a varied cross-section, along its length. This device includes a tip part, a flexible part, a tapering part and a manipulating part, with each part having its own structural characteristics. An x-ray impermeable material, such as a tungsten wire, is inserted into the hollow of the manipulating part for imparting proper toughness and rigidity to this part. The relatively complex, variable structure of the Yoshimura et al, guidewire is relatively difficult and expensive to manufacture. Further, Yoshimura, et al is not concerned with the anti-creep properties of the guidewire.

Beal U.S. Pat. No. 4,257,421 discloses a flexible rod formed by applying water soluble USP gelatin to a multi-strand nylon thread base in a spiral twist. The water soluble coating allows the rod to be removed from the tube, which it is used to place in a patient's body, by dissolving the gelatin. The gelatin coating, in its undissolved state is less flexible than the nylon thread base. Beal focuses on ease of removing the rod after use rather than on anti-creep and torque control properties.

There continues to be a need for a guidewire construction which has enhanced anti-creep properties, and preferably increased torque control.

SUMMARY OF THE INVENTION

A new composite structure useful in medical guidewire construction has been discovered. This structure has a reduced tendency to creep as opposed to previous guidewires, e.g., single plastic material guidewires, while being sufficiently soft, e.g., at its outer surface, to substantially avoid undue injury to the medical patient during use. Also, the structure preferably exhibits increased torque control properties.

In one broad aspect, the present structure comprises an elongated, flexible inner element and a substantially water insoluble, biocompatible sheath disposed over the inner element. The structure has a substantially uniform cross-section, e.g., as opposed to the variable cross-section of the guidewire described in the Yoshimura, et al patent noted above. In addition the structure is substantially solid, e.g., does not have the internal gaps inherent in the unbound filaments of the Herlitze stiffener, described above. For example, in the event the inner element comprises a plurality of filaments, e.g., monofilaments, it is preferred that such filaments be bonded together, thereby avoiding internal gaps which may lead to weak spots and/or loss in torque control.

The present structure is sized and shaped for insertion into the body of a medical patient. Thus, depending on the intended use of the guidewire, the cross-section of the present structure can be chosen to accommodate such intended use. The inner element has a reduced tendency to creep relative to the sheath, while the sheath has increased softness relative to the inner element. In this manner, the present structure is provided with anti-creep properties, e.g., from the inner element, while also having a biocompatible and relatively soft outer surface, e.g., from the outer sheath.

The term "guidewire" as used herein refers to any one of a multitude of components useful in placing various implements within the body of a medical patient. For example, such term includes guidewires, stiffening rods, introducers and the like which are useful in placing catheters, balloons and the like in the cardiovascular and other systems of medical patients. While the term "guidewire" is meant generally in this broad context, the present structure is particularly useful as a guidewire or stiffening rod in placing catheters.

The inner element has relatively high tensile strength. This feature aids in giving the present structure the desired degree of strength and stiffness, and also aids in achieving torque control. The inner element in general is less flexible than the outer sheath and preferably has a modulus in flexure of at least about five hundred thousand (500,000) pounds per square inch (psi), more preferably at least about one million (1,000,000) psi.

As noted above, in one embodiment the inner element is made up of a plurality of filaments which are preferably bonded together, to form a solid inner element. The individual filaments which make up the inner element may be made of the same material or different materials, preferably the same material, and may have the same cross-section area or different cross-sectional areas, preferably substantially the same cross-sectional area. The filaments may be made of any one or more suitable materials, provided that such filaments are capable of functioning as described herein.

The filaments are preferably made of a material selected from the group consisting of metal, glass, graphite, organic polymer and mixtures thereof. Each such monofilament preferably has a modulus in flexure similar to such modulus for the inner element as a whole.

In one particularly useful embodiment, the monofilaments are made of organic polymer materials, especially such materials which are commonly termed "liquid crystalline polymers". In another useful embodiment, the entire inner element is made of such liquid crystalline polymer materials. Such polymers are described in "Recent Advances in Liquid Crystalline Polymers", edited by L. Lawrence Chapoy, Elsevier Applied Science Publishers, London and New York (1985).

In brief, liquid crystalline polymers are materials which show a degree of crystallinity in the molten state. These materials are highly crystalline in the solid state, and often can be molecularly oriented, e.g., by extrusion, to form components having very high strengths. Among the liquid crystalline polymers are certain polyesters, polyamides and polyurethanes. The liquid crystalline polyesters include, for example, certain mono- and co-polyesters made from aromatic diols, aromatic dicarboxylic acids, and aromatic mono-hydroxy monocarboxylic acid compounds. Liquid crystalline polyamides include for example, poly (1,4-benzamide), poly(2,6-naphthalene, poly (trans-1,4-cyclohexylene), and poly (p,p'-biphenylene). One preferred group of liquid crystalline polymer for use in the present invention is one or more of the liquid crystalline polyesters.

The liquid crystalline polymer is preferably oriented relative to the longitudinal axis of the inner element. This can often be easily accomplished by extruding the liquid crystalline polymer inner element or the liquid crystalline polymer filament used in constructing the inner element. Such extrusion acts to orient the liquid crystalline polymer in the direction of the longitudinal axis of the inner element. This gives the inner element added strength and stiffness. This orientation is particularly effective in reducing the tendency of the present structure to creep.

The filaments included in the inner element, if any, are preferably bonded together, to form a substantially solid inner element. Although any suitable binding may be employed, it is preferred to use an organic polymeric material capable of wetting or intimately contacting the filaments as a binding agent. It is important to use an organic polymeric material capable of wetting the filaments so that all of the filaments are bonded together as a single composite. This adds strength to the present structure. The binding agent is chosen based on, for example, the monofilaments to be bound together and the nature of the outer sheath. Both thermoplastic and thermoset polymers may be employed. However, thermoset polymers are preferred because of their superior wetting properties. One particularly useful binding agent is a thermoset polymer system comprising a two part, unsaturated polyester, such as that sold under the trademark Polystal by Mobay Chemical Co.

In certain instances, it may be desirable to positively secure, preferably adhesively secure, the inner element to the outer sheath. Such securement may be accomplished in any suitable manner. For example, any suitable adhesive, which is compatible with both the inner element and the outer sheath, and has no substantial detrimental effect of the application in which the structure is used, may be employed. One particularly useful adhesive is an extrudable, hot melt adhesive material, such as various copolymers of ethylene and vinyl acetate. If an adhesive is employed it is preferably located between the inner element and the sheath and acts to adhesively secure the inner element to the sheath.

The elongated inner element may have any suitable, preferably a substantially uniform, cross-section. For example, the inner element may be circular, triangular, rectangular and the like in cross-section. The inner element preferably has a cross-section configuration which provides the structure with increased torque control relative to an inner element having a circular cross-section of the same area and made of the same material. In one particularly useful embodiment, the inner element is generally star shaped in cross-section. In another useful embodiment, the inner element has a cross-section such that a plurality of lobes extend outwardly from the center of the inner element. Such star shaped and multi-lobed inner elements have been found to provide increased torque control relative to an inner element have a circular cross-section of the same area and made of the same material. As noted above, torque control is highly desirable in order that the present structure can be manipulated, through an often tortuous path, to a desired location in the body of a medical patient.

The present sheath is biocompatible and has increased softness relative to the inner element. The sheath is biocompatible so that no undue adverse reaction is caused by the presence of the structure in the body of the medical patient. The relative softness of the sheath acts to avoid any undue trauma in the medical patient's body as a result of the movement of the structure. The sheath is also substantially water insoluble. Any suitable material may be used to construct the outer sheath. Examples of such materials include polyolefins, such as polyethylene, polytetrafluoroethylene, polyester-polyamide copolymers, polyurethanes and the like.

The present structure may be produced in any suitable manner. Extrusion, and in particular coextrusion of the inner element and sheath, is an especially useful method of producing the present structure. Extrusion is particularly preferred when the inner element is composed of one or more liquid crystal polymers, since the force of the extrusion process aids in orienting the liquid crystal polymer alone the longitudinal axis of the inner element, thus increasing the strength of the inner element.

These and other objects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a plan view of one embodiment of a medical-guidewire in accordance with the present invention.

FIG. 2 is an enlarged cross-section taken along line 2—2 of FIG. 1.

FIG. 3 is an enlarged cross-section of an alternate embodiment of the present structure.

DETAILED DESCRIPTION OF THE DRAWINGS

Figure 4:
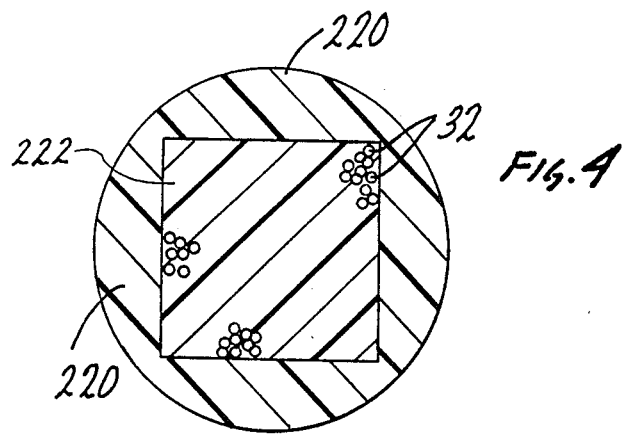
FIG. 4 is an enlarged cross-section of a further alternate embodiment of the present structure.

Referring to the drawings, and particularly to FIGS. 1 and 2, a new medical guidewire 10 is shown. Guidewire 10 includes a guidewire body 12, illustrated foreshortened for convenience, that extends from a proximal end portion 14 or within a proximal fitting 15 to a distal end portion 16 terminating at a distal end 18.

The guidewire body 12 has a substantially uniform cross-section from proximal end portion 14 to distal end portion 16. Guidewire body 12 includes a relatively soft outer sheath 20, a generally star-shaped (cross-section) inner element 22, and an adhesive layer 24 therebetween. Outer sheath 20 and inner element 22 are coaxial, that is these components have the same longitudinal axis. Outer sheath 20 is substantially water insoluble, biocompatible and is made of polyethylene. The relatively soft, biocompatible outer sheath allows the guidewire 10 to be introduced into the body of a medical patient without causing undue discomfort or trauma to the patient. Inner element 22 has a reduced tendency to creep relative to outer sheath 20. In the embodiment shown in FIGS. 1 and 2, inner element 22 is made of a liquid crystalline polyester polymer (LCPP). To add to the inherently high tensile strength of the LCPP, guidewire 10 is formed by extrusion. While being passed through the extrusion dye, the molecules of the LCPP become aligned or oriented relative to the longitudinal axis of the inner element 22. This orientation not only adds to the strength of the inner element 22, but also reduces the tendency of the inner element 22 to creep.

Adhesive layer 24 bonds outer sheath 20 to the inner element 22 and may be any suitable material capable of performing this function, e.g., an ethylene-vinyl acetate copolymer.

In the embodiment shown in FIGS. 1 and 2, inner element 22 has a star-shaped cross-section, while outer sheath has a generally circular cylindrically-shaped outer surface. The ribs 26a-f of the star shaped inner element 22 extend radially outwardly at equidistantly spaced apart locations from the center of inner element 22. The ribs 26a-f facilitate superior, e.g., more durable, bonding between outer sheath 20 and inner element 22. Further, ribs 26a-f provide guidewire 10 with increased torque control relative to a guidewire having a similar configuration but with an inner element having a circular cross-section.

Guidewire 10 is solid throughout and can be appropriately sized to form various functions, e.g., as a guidewire or stiffening rod to place a catheter in a desired location in the body of a medical patient, as an introducer to assist in introducing another implement of medical treatment equipment into the body of a medical patient and the like. Guidewire 10 has a very attractive combination of properties. It has a relatively simple structure which is substantially solid and easy to produce, e.g., by extrusion. The relatively soft, biocompatible outer sheath 20 allows guidewire 10 to be used in tortuous paths in the body of a medical patient without causing undue discomfort and trauma to the patient. Inner element 22 has substantial strength, thus reducing the risk of breakage. In addition, the anti-creep properties of the inner element 22 give the guidewire 10 the capability to be bent in various directions to successfully navigate through tortuous paths in medical patient's bodies. Further, the increased torque control of the inner element 22 allows one to maneuver guidewire 10 through such tortuous paths by applying torque forces to proximal end portion 14 and/or proximal fitting 15.

Another guidewire 110, constructed in accordance with the present invention, is illustrated in FIG. 3. Guidewire 110 employs an inner element 122 having a different cross-sectional shape than inner element 22 of guidewire 10, and no adhesive layer, comparable to adhesive layer 24 in guidewire 10, is utilized in guidewire 110. Otherwise, guidewire 110 is generally similar to guidewire 10 so that only the dissimilar aspects of guidewire 110 are described. For convenience, reference numerals in FIG. 3 are increased by one hundred over those designating similar features of guidewire 10 in FIGS. 1 and 2.

Inner element 122 of guidewire 110 has a triangular shaped cross-section. The three points 28a-c of the triangle are equidistantly spaced radially from the center of inner element 122. This triangularly shaped inner element 122 provides guidewire 110 with increased torque control relative to a guidewire having a similar inner element with a circular cross-section. Care should be exercised in selecting the materials used in outer sheath 120 and inner element 122 so that a satisfactory bond between these two elements, without a separate adhesive layer, is achieved.

Guidewire 110 functions in much the same manner as does guidewire 10.

Figure 5:
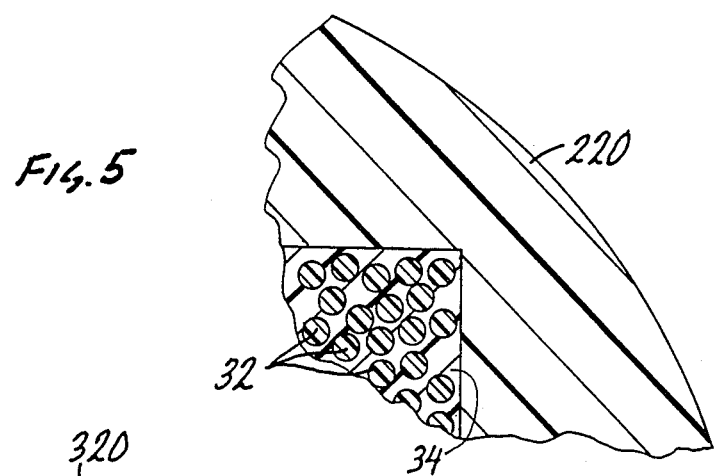
FIG. 5 is a further enlarged partial view of the cross-section of the embodiment of FIG. 4.

An additional guidewire 210, constructed in accordance with the present invention, is illustrated in FIGS. 4 and 5. Guidewire 210 employs an inner element 222 having a different construction and a different cross-sectional shape than inner element 22 of guidewire 10, and no adhesive layer, comparable to adhesive layer 24 in guidewire 10, is utilized in guidewire 210. Otherwise, guidewire 210 is generally similar to guidewire 10 so that only the dissimilar aspects of guidewire 210 are described. For convenience, reference numerals in FIGS. 4 and 5 are increased by two hundred over those designating similar features of guidewire 10 in FIGS. 1 and 2.

Inner element 222 of guidewire 210 has a square shaped cross-section. The four corners 30a-d of the square are equidistantly spaced radially from the center of inner element 222. A plurality of monofilaments 32, made from LCPP, are embedded in a thermoset polymeric material 34, such as a two part polyester system sold under the trademark Polystal by Mobay Chemical Company. The thermoset polymeric material 34 in the molten state has the ability to wet monofilaments 34 so that the inner element 222, made up of monofilaments 32 and thermoset polymeric material 34, is substantially solid with no significant gaps between any of the monofilaments 32 and the thermoset polymeric material 234. Preferably, the monofilaments 32 of LCPP are individually extruded to provide orientation along the longitudinal axis of the monofilament. Guidewire 210 can be produced by extrusion. In the embodiment shown in FIGS. 4 and 5, thermoset polymeric material 34 has the ability to bond to outer sheath 220 without a separate adhesive layer. However, it is within the scope of the present invention to include an adhesive layer, e.g., of ethylene-vinyl acetate copolymer adhesive, between outer sheath 220 and inner element 222 to provide bonding between these two components.

Guidewire 210 functions in much the same manner as does guidewire 10. The square cross-section of inner element 222 provides improved torque control relative to a similar inner element with a circular cross-section.

It should be noted that the LCPP monofilaments 32 can be replaced by monofilaments made of one or more other materials, such as metal, glass, graphite, organic polymer and the like. It is preferred that the monofilaments be bonded together to form a unitary, substantially solid inner element. This feature promotes strength and provides more consistent and predictable movement, e.g., in response to torque forces applied to proximal end portion 14 and a proximal fitting 15, as the guidewire is inserted into the body of a medical patient.

Figure 6:
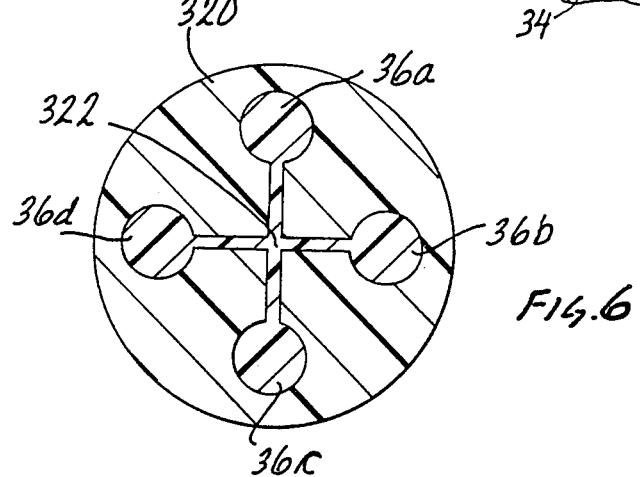
FIG. 6 is an enlarged view of the cross-section of another embodiment of the present invention.

Another guidewire 310, constructed in accordance with the present invention, is illustrated in FIG. 6. Guidewire 310 employs an inner element 322 having a different cross-sectional shape than inner element 22 of guidewire 10, and no adhesive layer, comparable to adhesive layer 24 of guidewire 10, is utilized in guidewire 310. Otherwise, guidewire 310 is generally similar to guidewire 10 so that only the dissimilar aspects of guidewire 310 are described. For convenience, reference numerals in FIG. 6 are increased by three hundred over those designating similar features of guidewire 10 in FIGS. 1 and 2.

Inner element 322 of guidewire 310 has a multilobed cross-section. The four lobes 36a–d of inner element 322 are equidistantly spaced radially from the center of inner element 310. This multi-lobed inner element 322 provides guidewire 310 with increased torque control relative to a guidewire having a similar inner element with a circular cross-section. Care should be exercised in selecting the materials used in the outer sheath 320 and inner element 322 so that a satisfactory bond between these two components, without a separate adhesive layer is achieved.

Guidewire 310 functions in much the same manner as does guidewire 10.

While this invention has been described with respect to various specific examples and embodiments, it is to be understood that the invention is not limited thereto and that it can be variously practiced within the scope of the following claims.

What is claimed is:

1. A medical guidewire comprising: an elongated, flexible inner element and a substantially water insoluble, biocompatible sheath disposed over said inner element, said medical guidewire having a substantially uniform cross-section, being substantially solid, and sized and shaped for insertion into the body of a medical patient, said inner element having a reduced tendency to creep relative to said sheath, and said sheath having increased softness relative to said inner element.

2. The structure of claim 1 wherein said inner element comprises a material selected from the group consisting of metal, glass, graphite, organic polymer and mixture thereof.

3. The structure of claim 1 wherein said inner element comprises a plurality of filaments which are bonded together.

4. The structure of claim 3 wherein said filaments are made of a material selected from the group consisting of metal, glass, graphite, organic polymer and mixtures thereof.

5. The structure of claim 3 wherein said filaments have modulus in flexure of at least about 500,000 psi.

6. The structure of claim 5 wherein said filaments have a modulus in flexure of at least about one million psi.

7. The structure of claim 3 wherein said monofilaments are made of organic polymer.

8. The structure of claim 7 wherein said organic polymer is at least one liquid crystalline polymer.

9. The structure of claim 8 wherein said liquid crystalline polymer is oriented relative to the longitudinal axis of said filament.

10. The structure of claim 8 wherein the liquid crystalline polymer is a polyester.

11. The structure of claim 3 wherein said filaments are bonded together by organic polymeric material.

12. The structure of claim 11 wherein said organic polymeric material is capable of wetting said filaments.

13. The structure of claim 11 wherein said organic polymeric material is a thermoset polymer.

14. The medical guidewire of claim 1 wherein said inner element has a modulus in flexure of at least about 500,000 psi.

15. The medical guidewire of claim 14 wherein said inner element has a modulus in flexure of at least about one million psi.

16. The medical guidewire of claim 1 wherein said inner element comprises organic polymer.

17. The medical guidewire of claim 1 wherein said inner element is secured to said sheath.

18. The medical guidewire of claim 1 wherein said inner element is adhesively secured to said sheath.

19. The medical guidewire of claim 1 which further comprises adhesive means located between said inner element and said sheath to adhesively secure said inner element to said sheath.

20. The medical guidewire of claim 19 wherein said adhesive means is an ethylene-vinyl acetate copolymer.

21. The medical guidewire of claim 1 wherein said inner element has a substantially uniform cross-section throughout.

22. The structure of claim 1 wherein said inner element is substantially rectangular in cross-section.

23. The structure of claim 1 wherein said inner element has a cross-section such that a plurality of lobes extend outwardly from the center of said inner element.

24. The structure of claim 1 wherein said sheath is made of a material selected from the group consisting of a polyester material, a polyurethane material, and a polyester-polyamide copolymer material.

25. A medical guidewire comprising: an elongated, flexible inner element made of at least one liquid crystalline organic polymer and a substantially water insoluble, biocompatible sheath disposed over said inner element, said medical guidewire having a substantially uniform cross-section, being substantially solid, and sized and shaped for insertion into the body of a medical patient, said inner element having a reduced tendency to creep relative to said sheath, and said sheath having increased softness relative to said inner element.

26. The medical guidewire of claim 25 wherein said liquid crystalline organic polymer is oriented relative to the longitudinal axis of said inner element.

27. The medical guidewire of claim 25 wherein the liquid crystalline organic polymer is a polyester.

28. A medical guidewire comprising: an elongated, flexible inner element having a cross-section which is other than circular in configuration and a substantially water insoluble, biocompatible sheath disposed over said inner element, said medical guidewire having a substantially uniform cross-section, being substantially solid, and sized and shaped for insertion into the body of a medical patient, said inner element having a reduced tendency to creep relative to said sheath, and said sheath having increased softness relative to said inner element.

29. The medical guide of claim 28 wherein said inner element is generally star shaped in cross-section.

* * * * *

UNITED STATES PATENT AND TRADEMARK OFFICE
CERTIFICATE OF CORRECTION

PATENT NO. : 4,867,174
DATED : September 19, 1989
INVENTOR(S) : Robert P. Skribiski It is certified that error appears in the above-identified patent and that said Letters Patent is hereby corrected as shown below:

Column 1, line 17 change "while,." to -- while, --

Column 4, line 63 change "alone" to -- along --.

Change "structure" to -- medical guidewire -- in the following instances:

Column 8, line 1
        Column 8, line 5
        Column 8, line 8
        Column 8, line 12
        Column 8, line 14
        Column 8, line 17
        Column 8, line 19
        Column 8, line 21
        Column 8, line 24
        Column 8, line 26
        Column 8, line 28
        Column 8, line 30
        Column 8, line 53
        Column 8, line 55
        Column 8, line 58

Signed and Sealed this

Twenty-ninth Day of January, 1991

*Attest:*

HARRY F. MANBECK, JR.

*Attesting Officer*      *Commissioner of Patents and Trademarks*